United States Patent [19]  [11] 3,985,870
Holstein  [45] Oct. 12, 1976

[54] TOOTHPASTES
[75] Inventor: Arthur G. Holstein, Waukegan, Ill.
[73] Assignee: Pfanstiehl Laboratories, Inc., Waukegan, Ill.
[22] Filed: Jan. 2, 1975
[21] Appl. No.: 537,900

Related U.S. Application Data
[63] Continuation-in-part of Ser. No. 127,781, March 24, 1971, abandoned.

[52] U.S. Cl. .................................... 424/57; 424/49
[51] Int. Cl.$^2$ .......................................... A61K 7/16
[58] Field of Search ................................ 424/49–58

[56] References Cited
UNITED STATES PATENTS
R15,691  9/1923  Pfanstiel .............................. 424/55

FOREIGN PATENTS OR APPLICATIONS
718,880  9/1965  Canada .................................. 424/52

Primary Examiner—Shep K. Rose
Attorney, Agent, or Firm—Wallenstein, Spangenberg, Hattis & Strampel

[57] ABSTRACT

Toothpaste which contains a polishing agent or abrasive in the form of a water-insoluble calcium compound, and a minor proportion of D-Glucoheptono-1:4-Lactone (Glucoheptono-γ-Lactone) to solubilize mucin plaque and to inhibit dental caries.

3 Claims, No Drawings

TOOTHPASTES

This application is a continuation-in-part of application Ser. No. 127,781, filed Mar. 24, 1971 now abandoned.

This invention relates to improved toothpastes which are particularly effective for solubilizing and washing away of accumulations of mucin plaque on teeth, gums and mouth tissues.

Numerous approaches have been made over a period of many years to control dental caries through the use of toothpastes. Most commonly such toothpastes and toothpowders, which, in addition to their contents, commonly, of polishing or abrasive ingredients in the form of water-insoluble calcium compounds, usually in conjunction with soaps or detergents, oxidizing agents and other supplemental ingredients, utilize such agents as fluorides, stannous salts and various other materials, function, in one manner or another, to inhibit or control dental caries.

The debris which collects on and between the teeth and gums in connection with chewing of foods is of a variety of different types depending, among other things, on the nature of the particular foods involved and the acidity or alkalinity conditions in the mouth. It has long been known that mucin in the saliva forms a coating or film on the teeth, gums and mouth tissues, and, where food particles or debris and bacteria are present in the mouth, such particles or debris and bacteria become mixed with the salivary mucin and collect on and between the teeth, the adhesive character of the mucin aiding in causing adhesion to and between the tooth surfaces. Depending upon the condition of alkalinity or acidity in the mouth, and possibly other factors, the mucin may be in the form of mucinates, and the plaque or film which forms contains mucinates. For convenience, the term "mucin" plaque will be understood to encompass the plaque whether it is composed of mucin proper and/or mucinates. The brushing of the teeth with toothpastes effects largely a physical removal of the mucin plaque and such associated food particles or debris as may be present, although the extent of such removal depends upon a number of other factors as well.

It has also heretofore been known that mucin plaque removal is enhanced by the presence of acids, and advantage of this fact has been taken by incorporating acids or acid-forming substances into dentifrices and mouth washes, considerable care, of course, being required to insure that the acids or acid-forming substances and the amounts thereof are so controlled as to insure against damage hazards to the mouth tissues as well as to the natural teeth. Fruit juice acids, vitamin C, citric acid, tartaric acid, lactic acid and other acids have been disclosed for such purposes.

Toothpastes have been marketed in the past which have contained as an ingredient thereof D-Galactono-1:4-Lactone in conjunction with precipitated chalk or precipitated calcium carbonte as polishing agent or abrasive. The purpose for the utilization of the D-Galactono-1:4-Lactone was to provide the toothpaste with a potential source of acid so that, in the presence of the saliva in the mouth, hydrolysis of said lactone would occur to form galactonic acid, a mild acid, as is disclosed in Reissue Pat. No. 15,691. The galactonic acid so formed effectively removed, loosened, or solubilized mucin plaque on the teeth, gums and mouth tissues so that said mucin plaque and any associated food particles or debris could readily be removed and washed away after brushing and rinsing. In use, in said toothpaste, the galactonic acid was only gradually formed because an equilibrium was set up whereby, as the formed galactonic acid was used up in the mouth or neutralized by the flow of saliva, the equilibrium was disturbed and then more of said lactone was immediately converted into galactonic acid thus maintaining the pH at a fairly constant level. The aforesaid toothpaste, while effective to loosen and remove or dissolve the mucin plaques, possessed certain serious disadvantages. One particular disadvantage of such toothpastes was that, when said lactone was hydrolyzed to galactonic acid, the latter would react with the precipitated calcium carbonate abrasive ingredient of the toothpaste to form calcium galactonate which was highly insoluble and caused a conversion of the toothpaste to a very stiff magma.

The present invention is based on the utilization of D-Glucoheptono-1:4-Lactone in toothpastes which contain a water-insoluble calcium salt as a polishing agent or abrasive. When D-Glucoheptono-1:4-Lactone is hydrolyzed by the saliva in the mouth or otherwise, it yields glucoheptonic acid which is effective to loosen, remove or dissolve mucin plaque. The glucoheptonic acid which is formed reacts with the calcium compound, such as precipitated calcium carbonate, to produce calcium glucoheptonate. However, calcium glucoheptonate is noncrystallizable and, therefore, the conversion of the toothpaste to a stiff magma, as occurred when D-Galactono-1:4-Lactone was used as in the previously known prior art in dentifrice compositions containing water-insoluble calcium compound polishing agents or abrasives, is avoided. Thus, the present invention makes feasible for the first time toothpastes containing such polishing agents or abrasives.

In the practice of the present invention, the D-Glucoheptono-1:4-Lactone is incorporated into toothpastes, in conjunction with a water-insoluble calcium compound polishing agent or abrasive. The D-Glucoheptono-1:4-Lactone can be used in variable proportions in the toothpastes, for instance, in the range of 0.5 or, better, 1 to 20%, but, generally, the proportions thereof will fall into the range of about 4 to 6% by weight of said toothpastes. Any conventional toothpaste formulations can be utilized in which the polishing agent or abrasive is a water-insoluble calcium compound, particularly desirable being those wherein the polishing agent or abrasive is precipitated calcium carbonate. Other calcium compounds which can be used alone or together with precipitated calcium carbonate, or in admixture with other polishing agents or abrasives, are dental grade calcium pyrophosphate, calcium orthophosphate, calcium metaphosphate, molecularly dehydrated calcium phosphates, tricalcium phosphate, dicalcium phosphate dihydrate, dicalcium phosphate anhydrous, and calcium sulfate. Of particular utility, in conjunction with the D-Glucoheptono-1:4-Lactone, are precipitated calcium carbonate, dicalcium phosphate dihydrate and tricalcium phosphate. Generally speaking, the calcium compounds will usually comprise at least about 25% and, more often, appreciably higher percentages, such as from about 40 to about 90% by weight of the toothpastes.

The following examples are illustrative but in no limitative of the invention since many other toothpastes can readily be made embodying the novel teachings of the present invention in light of the guiding principles and disclosures made herein.

| EXAMPLE 1 — TOOTHPASTE | PARTS |
|---|---|
| Precipitated calcium carbonate | 44 |
| Starch | 6.8 |
| Glycerine | 28 |
| Water | 14 |
| Lauryl sodium sulfate | 1 |
| D-Glucoheptono-1:4-Lactone | 5.2 |
| Flavoring | 1 |
| EXAMPLE 2 — TOOTHPASTE | PARTS |
| Precipitated calcium carbonate | 30 |
| Dicalcium phosphate | 10 |
| Glycerine | 25 |
| Water | 28 |
| Irish moss extract | 1.5 |
| D-Glucoheptono-1:4-Lactone | 5 |
| Flavoring | 0.5 |
| EXAMPLE 3 — TOOTHPASTE | PARTS |
| Dicalcium phosphate dihydrate | 27 |
| Insoluble sodium metaphosphate | 25 |
| Gum | 1.5 |
| Lauryl sodium sulfate | 1 |
| Glycerol | 39.5 |
| D-Glucoheptono-1:4-Lactone | 5 |
| Flavoring | 1 |
| EXAMPLE 4 — TOOTHPASTE | PARTS |
| Tricalcium phosphate | 53 |
| Gum | 1.5 |
| Lauryl sodium sulfate | 1.1 |
| Glycerol | 38.4 |
| D-Glucoheptono-1:4-Lactone | 5 |
| Flavoring | 1 |

What is claimed is:

1. A toothpaste containing at least 25% of a water-insoluble calcium compound polishing agent or abrasive selected from the group consisting of precipitated calcium carbonate, calcium pyrophosphate, calcium orthophosphate, calcium metaphosphate, molecularly dehydrated calcium phosphates, tricalcium phosphate, dicalcium phosphate dihydrate, dicalcium phosphate anhydrous, and calcium sulfate, free from D-Galactono-1:4-Lactone, said toothpaste being free from the tendency of conversion to a stiff magma formed from the reaction of said calcium compound as calcium galactonate formed from the galactonic acid yielded from hydrolysis of D-Galactono-1:4-Lactone, said toothpaste containing from 0.5 to 20% of D-Glucoheptono-1:4-Lactone, said percentages being by weight of said toothpaste, the reaction of said calcium compound with the glucoheptonic acid formed by hydrolysis of said D-Glucoheptono-1:4-Lactone being noncrystallizable whereby to prevent formation of a stiff magma in the toothpaste.

2. A toothpaste according to claim 1, in which said calcium compound constitutes from 40 to 90% of said toothpaste.

3. A toothpaste according to claim 1, in which the calcium compound is precipitated calcium carbonate and in which the D-Glucoheptono-1:4-Lactone is present in proportions in the range of about 4 to 6%.

* * * * *